(12) United States Patent
Piza Vallespir

(10) Patent No.: US 8,147,524 B2
(45) Date of Patent: Apr. 3, 2012

(54) INSTRUMENTATION AND METHODS FOR REDUCING SPINAL DEFORMITIES

(75) Inventor: Gabriel Piza Vallespir, Palma de Mallorca (ES)

(73) Assignee: Warsaw Orthopedic, Inc., Warsaw, IN (US)

( * ) Notice: Subject to any disclaimer, the term of this patent is extended or adjusted under 35 U.S.C. 154(b) by 1217 days.

(21) Appl. No.: 11/408,137

(22) Filed: Apr. 20, 2006

(65) Prior Publication Data

US 2006/0271050 A1 Nov. 30, 2006

Related U.S. Application Data

(63) Continuation of application No. PCT/US2006/010467, filed on Mar. 20, 2006.

(51) Int. Cl.
*A61B 17/88* (2006.01)

(52) U.S. Cl. ........ 606/279; 606/86 A; 606/246; 606/914

(58) Field of Classification Search ............ 606/54, 606/60, 246, 250, 251, 252, 253, 257, 260, 606/264, 265, 267, 279, 254–256, 258, 259, 606/261–263, 266, 268–278; 623/17.11, 623/17.15

See application file for complete search history.

(56) References Cited

U.S. PATENT DOCUMENTS

| | | | |
|---|---|---|---|
| 2,687,720 A * | 8/1954 | Haboush | 606/54 |
| 3,865,105 A * | 2/1975 | Lode | 606/54 |
| 4,078,559 A | 3/1978 | Nissinen | |
| 4,112,935 A | 9/1978 | Latypov et al. | |
| 4,274,401 A | 6/1981 | Miskew | |
| 4,361,141 A | 11/1982 | Tanner | |
| 4,361,144 A * | 11/1982 | Slatis et al. | 606/54 |
| 4,409,968 A | 10/1983 | Drummond | |
| 4,505,268 A | 3/1985 | Sgandurra | |
| 4,641,636 A * | 2/1987 | Cotrel | 606/250 |
| 4,854,304 A | 8/1989 | Zielke | |
| 5,102,412 A | 4/1992 | Rogozinski | |
| 5,219,349 A | 6/1993 | Krag et al. | |
| 5,261,908 A | 11/1993 | Campbell, Jr. | |
| 5,281,223 A | 1/1994 | Ray | |
| 5,391,168 A * | 2/1995 | Sanders et al. | 606/253 |
| 5,425,732 A | 6/1995 | Ulrich | |
| 5,478,340 A | 12/1995 | Kluger | |
| 5,531,747 A | 7/1996 | Ray | |
| 5,582,612 A * | 12/1996 | Lin | 606/250 |
| 5,591,165 A | 1/1997 | Jackson | |
| 5,591,167 A | 1/1997 | Laurain et al. | |

(Continued)

FOREIGN PATENT DOCUMENTS

DE 87 12 943 U1 11/1987

(Continued)

*Primary Examiner* — Eduardo C Robert
*Assistant Examiner* — Jerry Cumberledge

(57) ABSTRACT

Instrumentation and methods for reduction of a spinal deformity, including a plurality of elongate alignment elements and first and second reduction elements engaged to the alignment elements. Each of the alignment elements extends generally along a longitudinal axis and includes a proximal portion adapted for coupling to a corresponding vertebra and a distal portion. The first reduction element extends along a first transverse axis and is engaged with the distal portions of the alignment elements to maintain the distal portions in general alignment along the first transverse axis. The second reduction element extends along a second transverse axis and is movably engaged with the alignment elements wherein the proximal portions are positioned in general alignment along the second transverse axis as the second reduction element is displaced in a proximal direction to thereby reduce the spinal deformity.

52 Claims, 8 Drawing Sheets

U.S. PATENT DOCUMENTS

| | | | |
|---|---|---|---|
| 5,603,714 A | 2/1997 | Kaneda et al. | |
| 5,607,425 A | 3/1997 | Rogizinski | |
| 5,662,652 A * | 9/1997 | Schafer et al. | 606/261 |
| 5,702,392 A | 12/1997 | Wu et al. | |
| 5,720,751 A | 2/1998 | Jackson | |
| 5,797,910 A | 8/1998 | Martin | |
| 5,944,720 A | 8/1999 | Lipton | |
| 5,951,555 A | 9/1999 | Rehak et al. | |
| 6,214,004 B1 | 4/2001 | Coker | |
| 6,235,028 B1 * | 5/2001 | Brumfield et al. | 606/53 |
| 6,530,929 B1 * | 3/2003 | Justis et al. | 606/103 |
| 6,551,320 B2 | 4/2003 | Lieberman | |
| 6,565,568 B1 | 5/2003 | Rogozinski | |
| 6,648,888 B1 | 11/2003 | Shluzas | |
| 6,770,075 B2 | 8/2004 | Howland | |
| 6,790,209 B2 | 9/2004 | Beale et al. | |
| 6,805,716 B2 | 10/2004 | Ralph et al. | |
| 6,964,665 B2 | 11/2005 | Thomas et al. | |
| 7,285,121 B2 * | 10/2007 | Braun et al. | 606/279 |
| 2002/0138077 A1 | 9/2002 | Ferree | |
| 2002/0151895 A1 | 10/2002 | Soboleski et al. | |
| 2002/0173791 A1 * | 11/2002 | Howland | 606/61 |
| 2003/0088251 A1 | 5/2003 | Braun et al. | |
| 2004/0133207 A1 * | 7/2004 | Abdou | 606/73 |
| 2004/0172022 A1 * | 9/2004 | Landry et al. | 606/61 |
| 2005/0033291 A1 * | 2/2005 | Ebara | 606/53 |
| 2005/0033434 A1 * | 2/2005 | Berry | 623/17.14 |
| 2005/0209694 A1 * | 9/2005 | Loeb | 623/17.11 |
| 2005/0215999 A1 * | 9/2005 | Birkmeyer et al. | 606/61 |
| 2005/0234449 A1 * | 10/2005 | Aferzon | 606/61 |
| 2005/0245928 A1 * | 11/2005 | Colleran et al. | 606/61 |
| 2005/0288669 A1 * | 12/2005 | Abdou | 606/61 |
| 2006/0111712 A1 * | 5/2006 | Jackson | 606/61 |
| 2006/0111713 A1 * | 5/2006 | Jackson | 606/61 |
| 2006/0149236 A1 * | 7/2006 | Barry | 606/61 |
| 2006/0247630 A1 * | 11/2006 | Iott et al. | 606/61 |
| 2006/0264934 A1 * | 11/2006 | Fallin | 606/61 |

FOREIGN PATENT DOCUMENTS

| | | |
|---|---|---|
| DE | 38 07 335 A1 | 9/1989 |
| ES | 2201340 T3 | 3/2004 |
| FR | 2722393 A1 * | 1/1996 |
| JP | 10014934 A | 1/1998 |
| WO | WO 9829046 A1 * | 7/1998 |
| WO | WO 9844858 A1 * | 10/1998 |

* cited by examiner

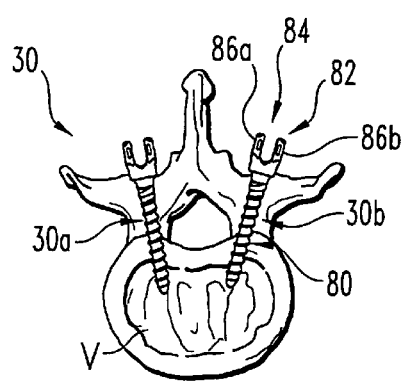
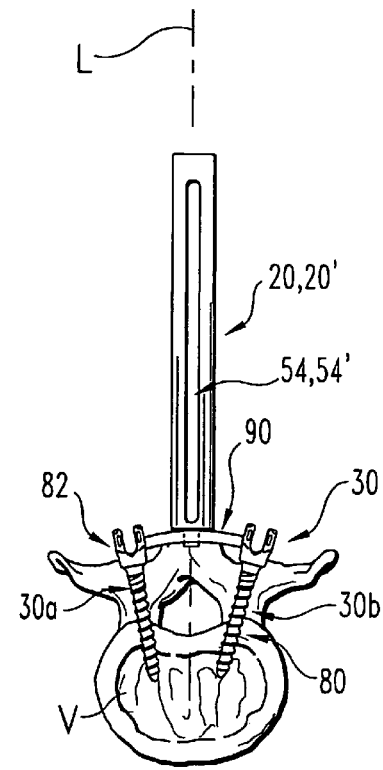
Fig. 17　　Fig. 18
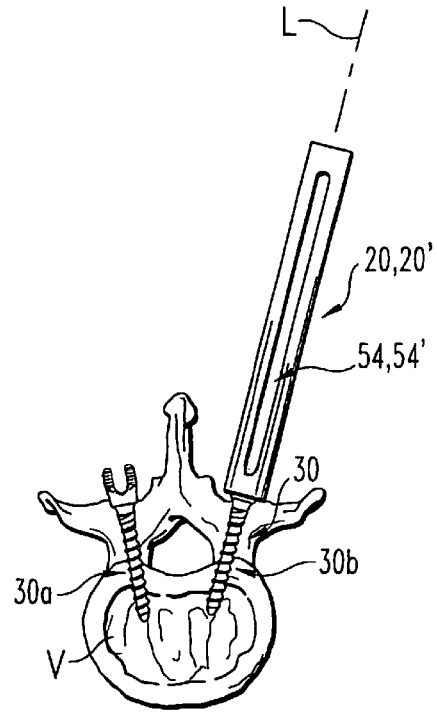
Fig. 19

INSTRUMENTATION AND METHODS FOR REDUCING SPINAL DEFORMITIES

CROSS REFERENCE TO RELATED APPLICATIONS

The present application is a continuation of International PCT Application No. PCT/US06/10467 filed Mar. 20, 2006 which claims foreign priority benefits under Title 35 U.S.C. §119 to Spanish Patent Application No. P200500734 filed Mar. 30, 2005, the entire contents of each application hereby being incorporated by reference.

FIELD OF THE INVENTION

The present invention relates generally to treatment of the spinal column, and more particularly relates to instrumentation and methods for reducing spinal deformities including, without limitation, scoliosis.

BACKGROUND

The normal anatomy of the spinal column presents different alignment and rotational characteristics along three spatial planes. In the coronal (or frontal) plane, the vertebrae are normally aligned and present no rotation. In the transverse (or axial) plane, the vertebrae are likewise normally aligned and present neutral rotation. In the sagittal plane, the vertebrae present a certain degree of rotation and translation which form the physiological curvature of the spine; namely, cervical lordosis, dorsa or thoracic kyphosis, and lumbar lordosis.

Spinal deformities of varying etiologies are well known. Such deformities include abnormal spinal curvatures, such as, for example, scoliosis, kyphosis, and/or other abnormal curvatures wherein natural alignment of the spine is altered. With specific regard to scoliotic deformities, the abnormal curvature of the spinal column is three-dimensional. Specifically, scoliotic deformities can be separated into abnormal translation and/or rotation of the vertebrae in each of the coronal, transverse and sagittal planes. Therefore, treatment of scoliosis should preferably be aimed at addressing reduction of the abnormal curvature in each of the three spatial planes.

A number of methods and techniques have been used to reduce abnormal spinal curvatures. Most of these techniques have been based on anchoring devices onto posterior elements of the spine (e.g., via clips or wires). Such techniques reduce the translational aspects of the deformity, but have little or no effect on the rotational aspects.

Additionally, pedicle screws have been used in the treatment of scoliosis, thereby raising the possibility of derotation of the spinal column. However, techniques for treatment of scoliosis using pedicle screws are based essentially on translation to align the spinal column, either by bending or rotating a spinal rod after the rod is engaged to the screws, or by forcing the pedicle screws into engagement with the rod. Other reduction techniques provide for derotation via the use the pedicle screws, but such derotation is usually implemented following placement of the spinal rod individually and consecutively into engagement with the pedicle screws. Additionally, when pedicle screws are anchored to a scoliotic spine, the screws follow the curvature of the spine and tend to be inclined in the transverse plane depending on vertebral rotation, thereby complicating placement of the spinal rods.

Treatment of a spinal deformity via a reduction technique to address both the alignment and rotational aspects of the deformity along all three spatial planes would be desirable.

Thus, there remains a need for improved instrumentation and methods for reducing spinal deformities. The present invention satisfies this need and provides other benefits and advantages in a novel and unobvious manner.

SUMMARY

The present invention relates generally to treatment of the spinal column, and more particularly relates to instrumentation and methods for reducing spinal deformities including, without limitation, scoliosis. While the actual nature of the invention covered herein can only be determined with reference to the claims appended hereto, certain forms of the invention that are characteristic of the preferred embodiments disclosed herein are described briefly as follows.

In one form of the present invention, instrumentation is provided for reduction of a spinal deformity, including a plurality of elongate elements, a first reduction element and a second reduction element. The elongate elements each extend generally along a longitudinal axis and include a proximal portion adapted for coupling to a corresponding vertebra and a distal portion. The first reduction element extends along a first transverse axis and is engaged with the distal portions of the elongate elements wherein the distal portions are maintained in general alignment relative to the first transverse axis. The second reduction element extends along a second transverse axis and is movably engaged with the elongate elements wherein the proximal portions are positioned in general alignment relative to the second transverse axis as the second reduction element is displaced in a proximal direction along the elongate elements to reduce the spinal deformity.

In another form of the present invention, instrumentation is provided for reduction of a spinal deformity, including a plurality of elongate elements, a first reduction element and a second reduction element. The elongate elements each extend generally along a longitudinal axis and include a proximal portion adapted for coupling to a corresponding vertebra and a distal portion. The first reduction element is engaged to the distal portions of the elongate elements to maintain the distal portions in a substantially fixed relationship relative to the first reduction element. The second reduction element is movably engaged to the elongate elements wherein displacement of the second reduction in a proximal direction results in relative movement of the proximal portions of the elongate elements to reduce the spinal deformity.

In another form of the present invention, instrumentation is provided for reduction of a spinal deformity, including a plurality of elongate elements, a first reduction element and a second reduction element. The elongate elements each include a proximal portion adapted for coupling to a corresponding vertebra and a distal portion, and each of the elongate elements defines a slot having a length extending between the proximal and distal portions. The first reduction element is engaged with the elongate elements to maintain the distal portions in general alignment along the first reduction element. The second reduction element is positioned within the slots defined by the elongate elements and is displaced along the length of the slots in a proximal direction to generally align the proximal portions of the elongate elements along the second reduction element to reduce the spinal deformity.

In another form of the present invention, instrumentation is provided for reduction of a spinal deformity, including a plurality of elongate elements, each extending generally along a longitudinal axis and including a proximal portion adapted for coupling to a corresponding vertebra and a distal portion. The instrumentation further includes means for coupling each of the elongate elements to a corresponding vertebra, means for maintaining the distal portions of the elongate elements in alignment generally along a first transverse axis, and means for aligning the proximal portions generally along a second transverse axis to reduce the spinal deformity.

In another form of the present invention, a method is provided for reducing a spinal deformity, including the steps of providing a plurality of elongate elements, each extending along a longitudinal axis and including a proximal portion and a distal portion, providing first and second reduction elements, coupling the proximal portions of the elongate elements to respective vertebrae, engaging the first reduction element with the elongate elements to maintain the distal portions of the elongate elements in general alignment relative to the first reduction element, engaging the second reduction element with the elongate elements, and displacing the second reduction element in a proximal direction to generally align the proximal portions of the elongate elements relative to the second reduction element to reduce the spinal deformity.

In another form of the present invention, a method is provided for reducing a spinal deformity, including the steps of providing a plurality of elongate elements, each extending along a longitudinal axis and including a proximal portion and a distal portion, coupling the proximal portions of the elongate elements to respective vertebrae, aligning the distal portions of the elongate elements generally along a first transverse axis, and aligning the proximal portions of the elongate elements generally along a second transverse axis while maintaining alignment of the distal portions to reduce the spinal deformity.

It is one object of the present invention to provide improved instrumentation and methods for reducing spinal deformities. Further objects, features, advantages, benefits, and aspects of the present invention will become apparent from the drawings and description contained herein.

BRIEF DESCRIPTION OF THE DRAWINGS

FIG. 17 is a schematical illustration of a vertebra with a pair of bone anchors bilaterally anchored to the vertebra.

FIG. 18 is a schematical illustration of the bone anchors shown in FIG. 17, with the bone anchors interconnected by a bridge member and with the alignment element shown in FIG. 7 engaged to the bridge member.

FIG. 19 is a schematical illustration of the bone anchors shown in FIG. 17, with the alignment element shown in FIG. 4 engaged directly to one of the bone anchors.

DESCRIPTION OF THE PREFERRED EMBODIMENTS

Figure 1:
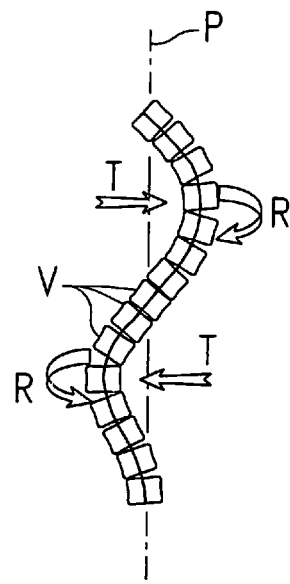
FIG. 1 is a schematical illustration of a scoliotic spine wherein the natural position and alignment of the vertebrae are altered due to abnormal vertebral translation and rotation.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 2:
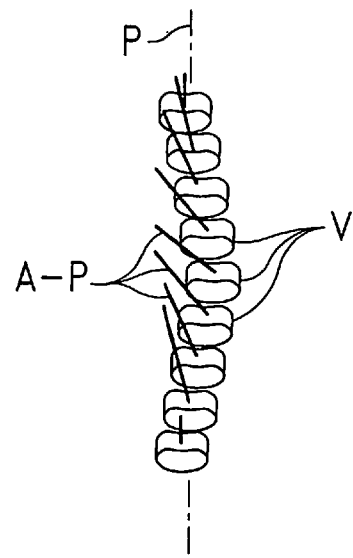
FIG. 2 is a schematical illustration of a scoliotic spine wherein the anteroposterior axes of the vertebrae are shown in a non-coplanar arrangement.

Referring to FIGS. 1 and 2, shown therein is a scoliotic spine including a number of vertebrae V. In a scoliotic spine, the natural position and alignment of the vertebrae V are altered due to abnormal vertebral rotation (depicted by arrows R) and abnormal vertebral translation (depicted by arrows T). As a result, the anteroposterior axes A-P of the vertebrae V, which are normally positioned within a common plane P (i.e., the sagittal plane), are non-coplanar (i.e., extend along multiple planes). Additionally, in a scoliotic spine, the thoracic spine is typically lordotic, thereby resulting in abnormal divergence of the anteroposterior axes A-P of the thoracic vertebrae which is less than the physiological divergence of the normal spinal anatomy.

Figure 3:
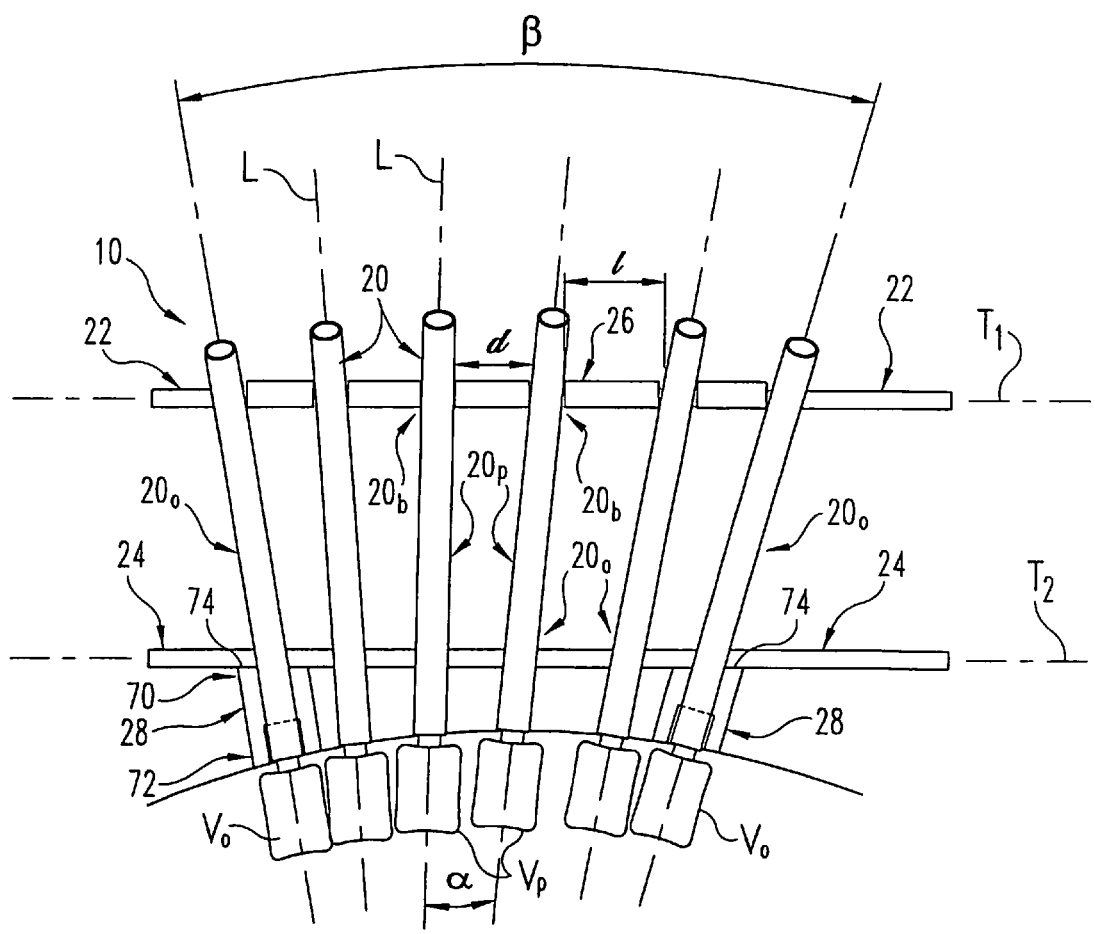
FIG. 3 is a schematical illustration of instrumentation for reducing a spinal deformity according to one form of the present invention.

Referring to FIG. 3, shown therein is instrumentation 10 according to one form of the present invention for use in treatment of the spinal column, and more particularly to reduce a spinal deformity. As will be discussed below, in one embodiment, the instrumentation 10 is used to treat abnormal curvatures of the spinal column, such as, for example, scoliosis. However, it should be understood that the present invention may also be used to treat other spinal deformities, including kyphotic deformities and other abnormal spinal curvatures.

In one form of the invention, the instrumentation 10 is configured to reposition and/or realign the vertebrae V along one or more spatial planes toward their normal physiological position and orientation. Preferably, the spinal deformity is reduced systematically in all three spatial planes of the spine, thereby tending to reduce surgical times and provide improved results. Although the present invention is illustrated and described in association with treatment of the spinal column, and more specifically to reduce abnormal spinal curvatures such as scoliosis or kyphosis, it should be understood that the present invention may also be used to treat other anatomic structures, and may be used to treat other spinal deformities or abnormalities. In one embodiment, the instrumentation 10 is used to provide three-dimensional reduction of a spinal deformity via a posterior surgical approach. However, it should be understood that the instrumentation 10 may be used via other surgical approaches, including, a lateral approach, an anterior approach, a posterolateral approach, an anterolateral approach, or any other surgical approach. Additionally, although FIG. 3 illustrates use of the instrumentation 10 to reduce a convex portion of a spinal curvature, it should be understood that the instrumentation 10 may also be used to reduce a concave portion of a spinal curvature, or to reduce both convex and concave portions of a spinal curvature, which is typically the case with regard to treatment of scoliosis.

In the illustrated embodiment of the invention, the instrumentation 10 generally includes a plurality elongate alignment elements or extenders 20 adapted for coupling to a number of vertebrae, a first elongate reduction element or rod 22 extending between and engaged with the alignment elements 20, a second elongate reduction element or rod 24 extending between and engaged with the alignment elements 20, a plurality of spacer elements 26 of select lengths coupled between adjacent pairs of the alignment elements 20, and a plurality of block elements 28 coupled to a number of the alignment elements 20 and positioned adjacent the vertebrae V. As will be discussed below, the elongate alignment elements 20 are coupled to corresponding vertebrae V via a number of bone anchor elements 30, such as, for example, bone screws (FIGS. 17-19). The elements of the instrumentation 10 are each formed of a biocompatible material, such as, for example, stainless steel or titanium. However, other materials are also contemplated, including, for example, titanium alloys, metallic alloys such as chrome-cobalt, polymer based materials such as PEEK, composite materials, or any other suitable material that would occur to one of skill in the art. Further details regarding the structure and function of each of the elements associated with the instrumentation 10 will be set forth below.

The elongate alignment elements 20 each extend generally along a longitudinal axis L and include a proximal portion 20a adapted for coupling to a corresponding vertebra V and an opposite distal portion 20b. As used herein, the term "proximal portion" means the portion of the alignment element 20 extending toward the spinal column, and may encompass one-half or more of the overall length of the alignment element. Similarly, the term "distal portion" means the portion of the alignment element 20 extending away the spinal column, which may likewise encompass one-half or more of the overall length of the alignment element. Accordingly, it should be understood that the term "proximal portion" is not limited to the proximal end portion of the alignment element, and the term "distal portion" is likewise not limited to the distal end portion of the alignment element. Additionally, although the longitudinal axes L along which the alignment elements 20 extend is illustrated as having a linear configuration, it should be understood that one or more of the longitudinal axes L may have a curved configuration, a curvilinear configuration, an angled configuration, a polygonal configuration, or any other suitable configuration. Furthermore, although the illustrated embodiment of the instrumentation 10 includes six alignment elements 20, it should be understood that the instrumentation 10 may includes any number of alignment elements 20.

The first elongate reduction rod 22 extends generally along a first transverse axis $T_1$ and is engaged with the alignment elements 20, and the second elongate reduction rod 24 extends generally along a second transverse axis $T_2$ and is likewise engaged with the alignment elements 20. As will be discussed in below, the first reduction rod 22 is engaged with the distal portions 20b of the alignment elements 20 to maintain the distal portions 20b in general alignment along the first transverse axis $T_1$. The second reduction rod 24 is axially displaced along the alignment elements 20 in a proximal direction from a position adjacent the distal portions 20b toward the proximal portion 20a, which in turn results in positioning of the proximal portions 20a in general alignment along the second transverse axis $T_2$. The alignment elements 20 act on the vertebrae V through the bone anchors 30 to reduce the spinal deformity via both translational and rotational movement of the vertebrae V, wherein the anteroposterior axes A-P of the vertebrae V are transitioned from an abnormal or non-coplanar state (FIGS. 2 and 20) toward a corrected or coplanar state (FIG. 25) wherein the anteroposterior axes A-P of the vertebrae V are positioned substantially within a common plane P, such as the sagittal plane.

Figure 6:
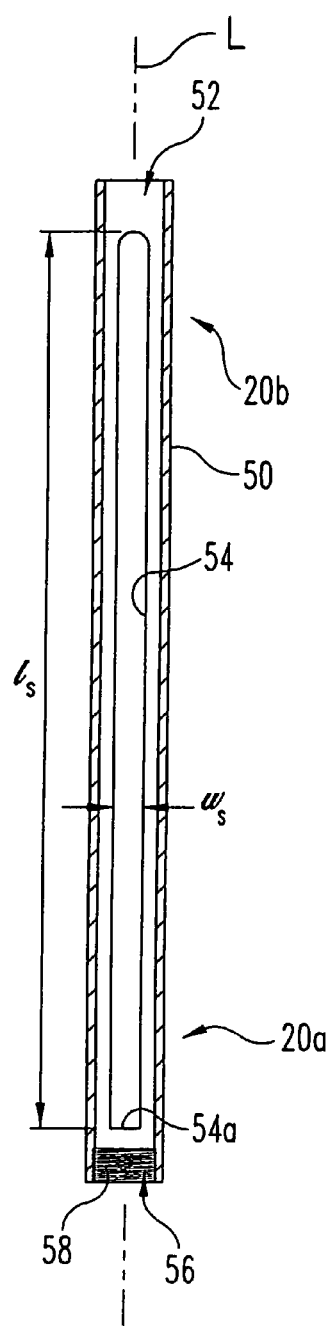
FIG. 6 is a cross-sectional side view of the elongate alignment element shown in FIG. 4, as viewed along line 6-6 of FIG. 4.
Figure 4:
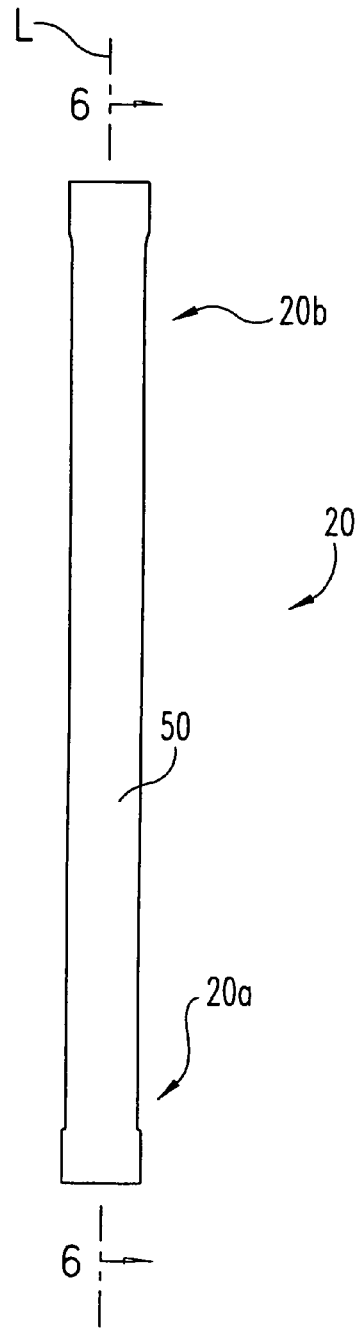
FIG. 4 is a side view of an elongate alignment element according to one embodiment of the present invention.
Figure 5:
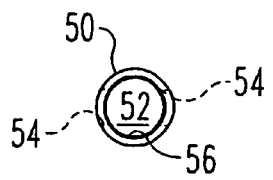
FIG. 5 is an end view of the elongate alignment element shown in FIG. 4.

Referring to FIGS. 4-6, shown therein is an elongate alignment element 20 according to one embodiment of the present invention. As indicated above, each of the alignment elements 20 extends generally along a longitudinal axis L and includes a proximal portion 20a and a distal portion 20b. As will be described below, the alignment element 20 is configured for releasable coupling to a bone anchor which is securely anchored to vertebral bone. When coupled to the bone anchor, a significant portion of the alignment element 20 extends outside of the patients body, thereby serving as an extension of the bone anchor, the purpose of which will be set forth below.

In the illustrated embodiment, the alignment element 20 has a generally cylindrical or tubular configuration including an outer wall 50 surrounding a hollow interior or axial passage 52 and defining a generally circular cross section. However, it should be understood that other shapes and configurations of the alignment element 20 are also contemplated as falling within the scope of the present invention, including a solid rod-like configuration, an elliptical or oval shape, a rectangular shape, a diamond shape, a polygonal shape, or any other suitable shape or configuration. In the illustrated embodiment, the alignment element 20 further includes a slot 54 extending transversely therethrough and having a slot length $l_s$ extending generally along the longitudinal axis L between the proximal and distal portions 20a, 20b. The slot 54 has a slot width $w_s$ that is preferably equal to or slightly less than an outer cross sectional dimension of the reduction rods 22 and 24. Although the slot 54 has been illustrated and described as having a particular size and configuration, it should be understood that other sizes and configurations of the slot 54 are also contemplated as falling within the scope of the present invention.

Additionally, the proximal portion 20a of the alignment element 20 defines an axial passage 56 defining internal threads 58. The internal threads 58 are adapted for threading engagement with a corresponding portion of a bone anchor, or to an element coupled to one or more bone anchors, to releasably couple the alignment element 20 to the one or more bone anchors and to the vertebra. In a specific embodiment, the internal threads 58 are engaged with a threaded projection associated with a bone screw, such as, for example, an externally threaded nut used with a pedicle screw. One such embodiment is present in the Synergy™ Spinal System manufactured by Interpore Cross International of Irvine, Calif. However, it should be understood that other structures and techniques for releasably coupling the alignment elements 20 to the bone anchors are also contemplated. Additionally, it should be understood that the alignments elements 20 may be adapted for coupling with other types of bone anchors and other configurations of bone screws. It should further be understood that engagement of the alignment elements 20 directly to the vertebrae V is also contemplated as falling within the scope of the present invention.

As will be discussed in greater detail below, the axial slot 54 in the alignment elements 20 is sized and configured to receive the first reduction rod 22 therein adjacent the distal portions 20b to align the distal portion 20b of the alignment elements 20 generally along the first transverse axis $T_1$, and to maintain the distal portions 20b in general alignment along the first transverse axis $T_1$. In the illustrated embodiment, the first reduction rod 22 is engaged with each of the alignment elements via positioning of the reduction rod 22 within the axial slots 54. However, in other embodiments, the first reduction rod 22 may be positioned within a separate opening or passage extending through the distal portions 20b of the alignment elements 20. In still other embodiments, the first reduction rod 22 may be engaged with each of the alignment elements 20 via other connection techniques, such as, for example, by forming openings along the length of the reduction rod 22 for receiving the distal portions 20b of the alignment elements 20 therein, or by providing a number of connector or coupler mechanisms engaged between the alignment elements 20 and the reduction rod, or by other suitable structures and techniques for engaging the reduction rod 22 to the alignment elements 20 to align and maintain alignment of the distal portions 20b generally along the transverse axis $T_1$.

The axial slot 54 in the alignment elements 20 is also sized and configured to receive the second reduction rod 24 therein to allow axial displacement of the second reduction rod 24 through the slot 54 in a proximal direction from a position adjacent the distal portion 20b toward the proximal portion 20a. As will be discussed below, sliding engagement of the second reduction rod 24 through the slots 54 in the alignment elements 20 draws the proximal portions 20a of the alignment elements 20 into general alignment with one another along the second transverse axis $T_2$.

In the illustrated embodiment, the second reduction rod 24 slidably engages each of the alignment elements 20 via axial displacement of the reduction rod 24 through the slots 54. However, in other embodiments, the second reduction rod 24 may be engaged with the alignment elements 20 via other connection techniques, such as, for example, by forming openings along the length of the reduction rod 24 for receiving the alignment elements 20 therein and by slidably engaging the reduction rod 24 along an exterior surface of the alignment elements 20. In another embodiment, the second reduction rod 24 may be coupled to the alignment elements 20 via a number of rings or collars, or other types of connectors or coupler mechanisms, which are slid along an exterior surface of the alignment elements 20. It should be understood that other suitable devices and techniques for slidably engaging the reduction rod 24 along the alignment elements 20 to align the proximal portions 20b generally along the transverse axis $T_2$ are also contemplated as falling within the scope of the present invention.

Figure 9:
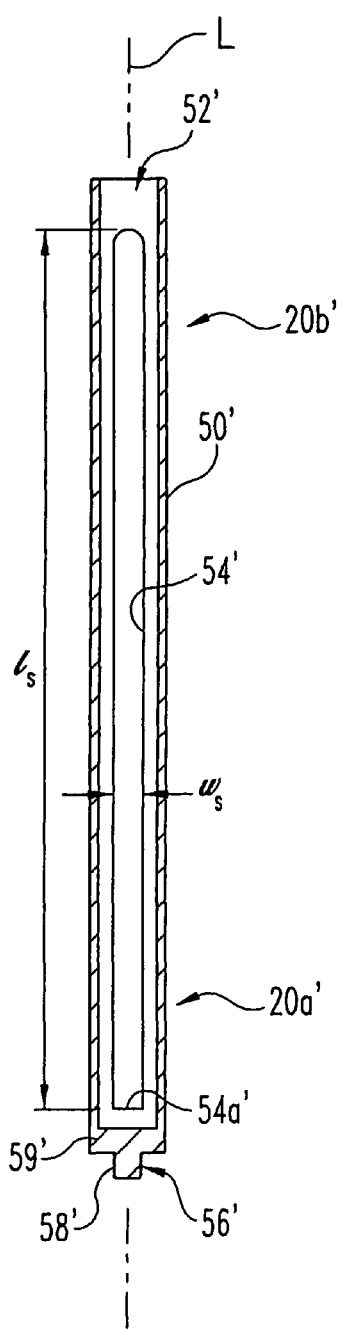
FIG. 9 is a cross-sectional side view of the elongate alignment element shown in FIG. 7, as viewed along line 9-9 of FIG. 7.
Figure 7:
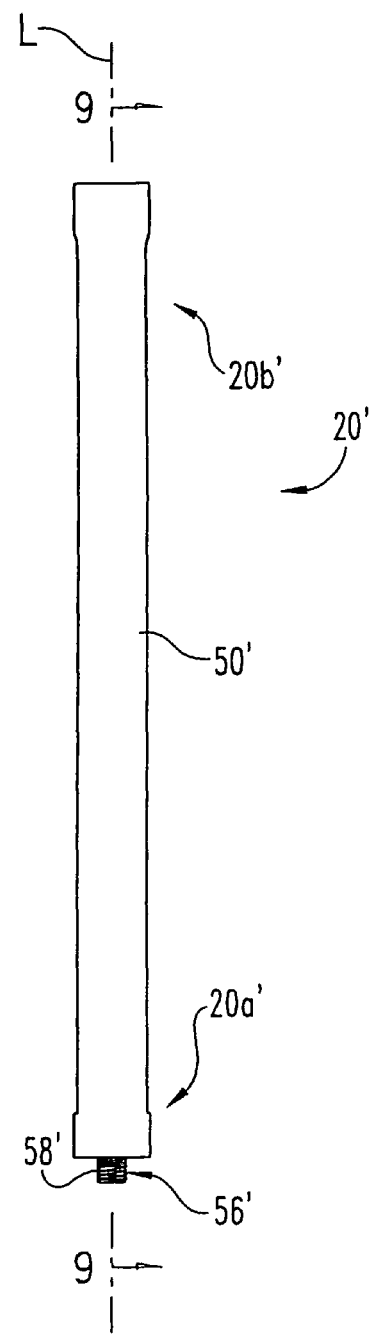
FIG. 7 is a side view of an elongate alignment element according to one embodiment of the present invention.
Figure 8:
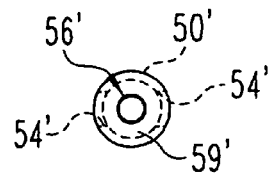
FIG. 8 is an end view of the elongate alignment element shown in FIG. 7.

Referring to FIGS. 7-9, shown therein is an elongate alignment element 20' according to another embodiment of the present invention. The alignment element 20' is configured similar to the alignment element 20 illustrated and described above, extending generally along a longitudinal axis L, including proximal and distal portions 20a' and 20b', and having a generally cylindrical configuration including an outer wall 50' surrounding a hollow interior or axial passage 52'. The alignment element 20' likewise includes a slot 54' extending transversely therethrough and having a slot length $l_s$ and a slot width $w_s$. The axial slot 54' is sized and configured to receive the first and second reduction rods 22, 24 therein in a manner similar to that described above with regard to the alignment element 20.

However, unlike the alignment element 20 which defines internal threads 58 extending along an axial passage 56, the distal portion 20b' of the alignment element 20' defines an axial stem or projection 56' defining external threads 58', with the axial stem 56' extending from a closed distal end wall 59'. The external threads 58' are adapted for threading engagement with a corresponding portion of a bone anchor, or to an element coupled with one or more bone anchors, to releasably couple the alignment element 20' to the one or more bone anchors and to the vertebra. In a specific embodiment, the externally threaded stem 56' is engaged within a threaded passage associated with a bone screw, such as, for example, within the head of a pedicle screw. One such embodiment of a pedicle screw is used in association with the CD-Horizon® Legacy™ Spinal System manufactured by Medtronic Sofamor Danek of Memphis, Tenn. However, the use of other types and configuration of bone anchors and bone screws in association with the instrumentation 10 is also contemplated as falling within the scope of the present invention. It should also be understood that the internal or external threads 58, 58' associated with the alignment elements 20, 20' may be adapted for threading engagement with various types of bone anchors or bone screws used in association with the instrumentation 10.

In other embodiments of the invention, the alignment elements may be provided with a first type of connection mechanism at one end of the alignment element, and a second type of connection mechanism at the opposite end of the alignment element, thereby providing increased versatility to the instrumentation 10. For example, in one embodiment, one end of the alignment element may be provided with an internally threaded passage similar to that illustrated and described above with regard to the alignment element 20, with the opposite end provided with an externally threaded stem similar to that illustrated and described above with regard to the alignment element 20'.

In specific embodiments of the invention, the alignment elements 20, 20' have an external diameter of about 15 mm, an internal diameter of about 12 mm, and an overall length between about 180 mm and 210 mm. Additionally, the axial slots 54, 54' extending through the alignment elements 20, 20' have a slot width $w_s$ of about 6.5 mm and a slot length $l_s$ between about 160 mm and 180 mm, thereby leaving about 10 mm of wall length at each end of the closed slots 54, 54'. However, it should be understood that other dimensions of the structures and features associated with the alignment elements 20, 20' are also contemplated as falling within the scope of the present invention. Additionally, in one embodiment of the invention, each of the alignment elements 20, 20' used in association with the instrumentation 10 have substantially the same overall length. However, in other embodiments, the alignment elements 20, 20' may be provided with different overall lengths.

Figure 10:
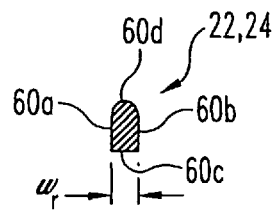
FIG. 10 is a cross-sectional view of a reduction element according to one embodiment of the present invention.

Referring to FIG. 10, in one embodiment of the invention, each of the first and second reduction rods 22 and 24 is configured as a substantially solid rod defining a generally rectangular outer profile having a pair of substantially planar side surfaces 60a, 60b, a substantially planar lower surface 60c, and a rounded or semi-circular upper surface 60d. However, it should be understood that the reduction rods 22 and 24 can take on other shapes and configurations. For example, the reduction rods 22 and 24 need not necessarily have a generally rectangular outer profile, but can instead have a circular shape, an elliptical or oval shape, a diamond shape, a polygonal shape, an irregular or any other suitable shape or configuration.

Additionally, the reduction rods 22 and 24 need not necessarily be solid, but can have a tubular configuration defining a hollow interior. In one embodiment, the reduction rods 22 and 24 define a rod width $w_r$ that is sized in relatively close tolerance with the width $w_s$ of the slot 54, 54' in the alignment elements 20, 20', while still allowing movement of the reduction rods 22, 24 into and through the slot 54, 54'. In a specific embodiment, the first and second reduction rods 22, 24 each have a rod width $w_r$ of about 6.5 mm. However, other sizes are also contemplated as falling with the scope of the present invention. Furthermore, although the transverse axes $T_1, T_2$ along which the reduction rods 22, 24 extend have been illustrated as having a linear configuration, it should be understood that one or both of the transverse axes $T_1, T_2$ may have a curved configuration, a curvilinear configuration, an angled configuration, a polygonal configuration, or any other suitable configuration. For example, in an alternative embodiment of the invention, one or both of the reduction rods 22 and 24 may provided with a predetermined curvature to achieve a different degree of correction of an abnormal spinal curvature. Additionally, providing one or both of the reduction rods 22 and 24 with a predetermined curvature may be beneficial in achieving limited or partial reduction of a relatively stiff abnormal spinal curvature. Furthermore, although the first and second reduction elements 22 and 24 have been illustrated and described as rods, it should be understood that other configurations of the first and second reduction elements 22 and 24 are also contemplated, such as, for example, plates, tubes, cables or any other elongate structure suitable for engagement with the alignment elements 20, 20'.

Figure 11:
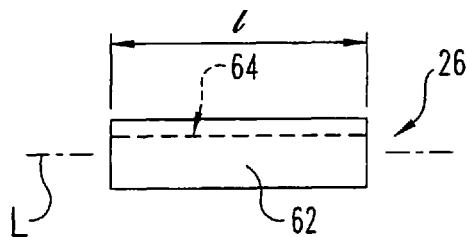
FIG. 11 is a side view of a spacer element according to one embodiment of the present invention.
Figure 12:
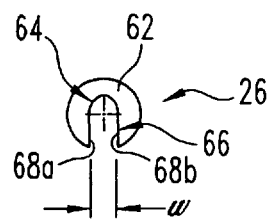
FIG. 12 is an end view of the spacer element shown in FIG. 11.

Referring to FIGS. 11 and 12, shown therein is a spacer element 26 according to one embodiment of the present invention. In the illustrated embodiment, the spacer elements 26 extends along a longitudinal axis L and has a generally cylindrical or tubular configuration defining a generally circular outer cross section and including an outer wall 62 surrounding a hollow interior or axial passage 64. The spacer element 26 also defines a slot 66 extending along the entire length l of the spacer element 26 and communicating between an exterior surface of the outer wall 62 and the axial passage 64. The slot 66 defines an open end for transversely receiving the reduction rod 22 into the axial passage 64, with the slot 66 and/or the axial passage 64 defining one or more substantially flat or planar surfaces 68a, 68b that are engaged with the planar side surfaces 60a, 60b of the reduction rod 22 to prevent rotation of the spacer element 26 relative to the reduction rod 22. Additionally, the inner profile of the axial passage 64 and/or the slot 66 may be sized in relatively close tolerance with, and possibly slightly smaller than, the outer profile of the reduction rod 22 to retain the spacer element 26 on the reduction rod 22 via a friction or interference fit. Furthermore, an outer surface of the reduction rod 22 and/or one or more of the inner surfaces defining the axial passage 64 and/or the slot 66 may be roughened to further facilitate retention of the spacer element 26 on the reduction rod 22. In an alternative embodiment, the spacer element 26 may define a closed axial passage 64 (e.g., without the slot 66), with the reduction rod 22 being axially inserted through the axial passages 64 in the spacer elements 26.

The spacer elements 26 have select lengths l and, as illustrated in FIG. 3, are engaged between the distal portions of adjacent pairs of the alignment elements 20p to space the adjacent distal end portions apart at a select distance d. The ends of the spacer elements 26 may be shaped or contoured to match the outer profile of the alignment elements 20, 20' to provide more secure and stable engagement therebetween. Alternatively, the ends of the spacer elements 26 may be provided with features that are engaged with corresponding features of the adjacent alignment elements 20p. In one embodiment, a spring-loaded ball and detent arrangement may be provided. In other embodiments, a tongue-and-groove arrangement may be provided. As will be discussed below, with the proximal portions of the adjacent pair of alignment elements 20p securely coupled to adjacent vertebrae Vp, spacing the distal portions apart at a select distance d correspondingly positions the adjacent pairs of vertebrae Vp at an angle α, which preferably corresponds to the correct physiological angular orientation of the adjacent vertebrae Vp (e.g., the kyphosis angle) along the sagittal plane.

Although the spacer elements 26 have been illustrated and described as being configured for coupling to the first reduction rod 22, it should be understood that in other embodiments of the invention, the spacer elements 26 may alternatively be engaged directly to the alignment elements 20, 20' to space the adjacent distal portions apart at the select distances d, and need not necessarily be coupled to the reduction rod 22. Additionally, the spacer elements 26 may be engaged to other portions of the alignment elements 20, 20', including engagement within the slots 54, 54' in the alignment elements 20, 20'. Furthermore, although the spacer elements 26 have been illustrated and described as having a hollow, tubular configuration which defines a generally circular cross section, other shapes and configurations are also contemplated as falling within the scope of the present invention, including a solid rod-like configuration, an elliptical or oval shape, a rectangular shape, a diamond shape, a polygonal shape, or any other shape or configuration suitable to space the distal end portions of the adjacent pairs of alignments elements 20p apart at the select distance d to correspondingly position the adjacent vertebrae Vp at a select angle α, which preferably substantially corresponds to the natural physiological angle between the adjacent vertebrae Vp.

Additionally, in other embodiments of the invention, the spacer elements may be configured as a plate-like or bar-like member defining openings that are sized to receive the distal ends of an adjacent pair of the alignment elements therein to space the adjacent distal portions apart at a select distance d. In another embodiment, the spacer element may include rings or collars or rings that are interconnected by a bridge member and positioned over the distal ends of an adjacent pair of the alignment elements to space the adjacent distal portions apart at a select distance d. In still other embodiments, the spacer element may be configured as a frame which engages three or more of the alignment elements to space the adjacent distal portions of the alignment elements apart at select distances d.

In the illustrated embodiment, the spacer elements 26 are each provided with a predetermined length l which may be calculated by analyzing the specific geometric features and characteristics associated with the adjacent pair of vertebrae Vp when normally aligned and positioned, and the specific features and characteristics associated with the instrumentation 10 including the dimension characteristics of the alignment elements 20. However, in other embodiments of the invention, the spacer elements 26 may be configured such that the overall spacer length is variable/adjustable to provide a select length l to space the adjacent distal portions 20b of the alignment elements 20 apart at a select distance d and to correspondingly position the adjacent vertebrae Vp at an angle α corresponding to the correct physiological angular orientation of the adjacent vertebrae Vp along the sagittal plane. Adjustment of the spacer elements 26 to the appropriate lengths l may be performed prior to the surgical procedure, or may be performed intra-operatively.

In one embodiment, each of the spacer elements 26 may be formed as a multi-piece assembly including two or more axial portions or segments that are arranged in stacked relation to provide a spacer element having a select overall length l. In another embodiment, each of the spacer elements 26 may include two or more axial portions or segments that are axially displaceable relative to one another and which may be locked in position to provide a spacer element having a select overall length l. In a specific embodiment, the spacer element 26 may be provided with a turnbuckle configuration wherein the overall spacer length l may be adjusted via threading engagement between two or more of the axial sections. In another specific embodiment, a spacer element 26 may be provided with a ratcheting configuration wherein the overall spacer length l may be adjusted in a first direction (e.g., a separation direction) while preventing adjustment in a second direction (e.g., a collapsing direction).

Figure 13:
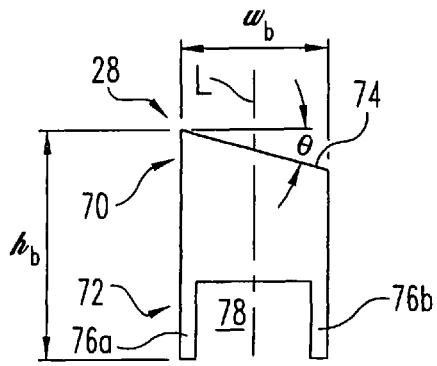
FIG. 13 is a side view of a block element according to one embodiment of the present invention.
Figure 14:
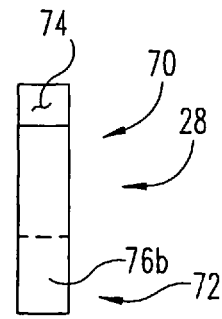
FIG. 14 is an end view of the block element shown in FIG. 13.
Figure 15:
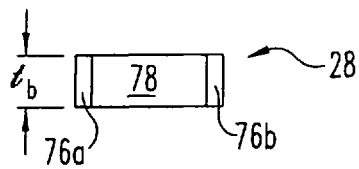
FIG. 15 is a bottom view of the block element shown in FIG. 13.

Referring to FIGS. 13-15, shown therein is a block element 28 according to one embodiment of the present invention. In the illustrated embodiment, the block element 28 has a monolithic configuration extending generally along a longitudinal axis L and defining a block height $h_b$, a block width $w_b$, and a block thickness $t_b$. Additionally, the block element 28 includes an upper portion 70 and a lower portion 72. The upper portion 70 of the block element 28 defines an upper engagement surface 74 that is angled at a taper angle θ relative to a reference axis arranged perpendicular to the longitudinal axis L. The lower portion 72 of the block element 28 includes a pair of legs 76a, 76b extending generally along the longitudinal axis L and defining a space or cavity 78 therebetween.

Figure 16:
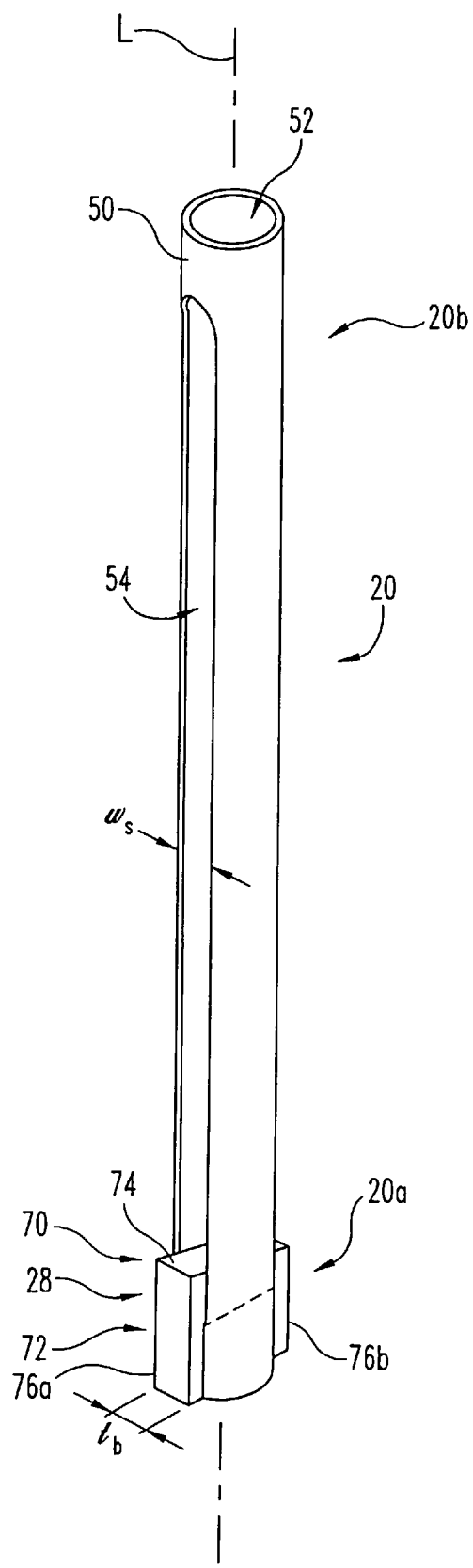
FIG. 16 is a side perspective view of an assembly including the block element shown in FIG. 13 engaged with the alignment element shown in FIG. 4.

As shown in FIG. 16, the block element 28 is engagable with the alignment element 20 in such a manner as to arrange the tapered engagement surface 74 in general alignment with the slot 54 extending transversely through the alignment element 20. The block element 28 has a block thickness $t_b$ that is equal to or slightly less than the slot width $w_s$ such that the block element 28 may be transversely received within the slot 54, with the space 78 between the legs 76a, 76b positioned to receive a proximal portion of the alignment element 20 therein, and with the legs 76a, 76b extending along an exterior surface of the outer wall 50 to maintain engagement of the block element 28 with the alignment element 20.

As shown in FIG. 3, block elements 28 having a select block height $h_b$ and a select taper angle θ are engaged to each of the outer alignment elements 20o, with the taper angle inwardly tapering toward the central portion of a convex spinal curvature. Alternatively, if the instrumentation 10 is used in the treatment of a concave spinal curvature, the block elements 28 may be arranged such that the taper angle θ outwardly tapers away from the concave spinal curvature. The outer alignment elements 20o are in turn anchored to the outer vertebrae Vo which define the outer ends or limits of a convex (or concave) portion of the spinal curvature being treated.

In the illustrated embodiment, the spinal curvature being treated is a kyphotic curvature having a convex configuration facing a posterior direction. However, in other embodiments, the spinal curvature being treated may comprise a lordotic curvature having a concave configuration facing a posterior direction. As will be discussed below, the lower surface of the reduction rod 24 engages the tapered surfaces 74 of the block elements 28 as the reduction rod 24 is axially displaced in a proximal direction through the slots 54 in the alignment elements 20, which in turn results in positioning of the outer alignment elements 20o and the corresponding outer vertebrae Vo at a select height and at a select angular orientation relative to one another, which preferably corresponds to the normal physiological height and angular orientation (e.g., the natural kyphosis angle) of the vertebrae Vo along the sagittal plane. In this manner, the block elements 28 allow relative translation (e.g., sinking) of the outer vertebrae Vo along the sagittal plane to position the outer vertebrae Vo at a substantially normal physiological height. Additionally, the block elements 28 allow relative rotation of the outer vertebrae Vo along the sagittal plane to position the outer vertebrae Vo at an angle β relative to one another which preferably substantially corresponds to the normal physiological angle of the outer vertebrae Vo.

Although the block elements 28 have been illustrated and described as having a particular shape and configuration, it should be understood that other shapes and configurations of the block element 28 are also contemplated as falling within the scope of the present invention. In one embodiment, the block elements 28 used in association with the outer alignment elements 20o are configured substantially identical to one another. However, in other embodiments, the block elements 28 may have different configurations. It should be understood that the configuration of each block element 28 is selected to provide a particular physiological angle β between the outer vertebrae Vo. In this regard, the overall block height $h_b$ and the taper angle θ associated with the upper engagement surface 74 are particularly relevant in establishing a physiological height and angle β between the outer vertebrae Vo which form the boundaries of at least a portion of the spinal curvature being treated (e.g., dorsal kyphosis). Although the instrumentation 10 shown in FIG. 3 utilizes a pair of block element 28 engaged with the outer alignment elements 20o (which are in turn anchored to the outer vertebrae Vo), it should be understood that block elements 28 may be used in association with other alignment elements 20, including one or more of the intermediate alignment elements 20 positioned between the outer alignment elements 20o.

In an alternative embodiment of the invention, block elements 28 are not necessarily required for use in association with the instrumentation 10. Instead, the slot 54, 54' defined by the alignment element 20, 20' may include a distally-facing engagement surface 54a, 54a' (FIGS. 6 and 9) that is tapered at an angle θ relative to a reference axis arranged generally perpendicular to the longitudinal axis L, thereby eliminating the requirement for separate block elements 28. As should be appreciated, in such an alternative embodiment, the reduction rod 24 may be engaged directly against the engagement surface 54a, 54a' to correspondingly position the outer vertebrae Vo at the desired physiological height and angle β.

In one specific embodiment, the block element 28 has a block height $h_b$ of about 30 mm, a block width $w_b$ of about 20 mm, a block thickness $t_b$ of about 6.5 mm, a width of the space 78 between the legs 76a, 76b of about 15 mm, and a taper angle θ associated with the upper engagement surface 74 of about 15 degrees. In another specific embodiment, the block element 28 has a block height $h_b$ of about 20 mm, a block width $w_b$ of about 20 mm, a block thickness $t_b$ of about 6.5 mm, a width of the space 78 between the legs 76a, 76b of about 15 mm, and a taper angle θ associated with the upper engagement surface 74 of about 7.5 degrees. However, it should be understood that other dimensions of the structures and features associated with the block elements 28 are also contemplated as falling within the scope of the present invention.

Having illustrated and described the elements and features associated with the instrumentation 10, reference will now be made to a method for reducing a spinal deformity according to one form of the present invention. Referring to FIG. 17, shown therein are bone anchors 30 engaged to a vertebra V in a bilateral arrangement along each side of the spinal column. In the illustrated embodiment, a pair of bone anchors 30a, 30b is anchored to a single vertebra V. However, it should be understood that a pair of bone anchors 30a, 30b is engaged to each of a plurality of vertebrae V along the portion of the spinal column being treated. It should further be understood that in other embodiments, a single bone anchor 30 or three or more bone anchors 30 may be engaged to each of a plurality of vertebrae V along the portion of the spinal column being treated.

Figure 26:
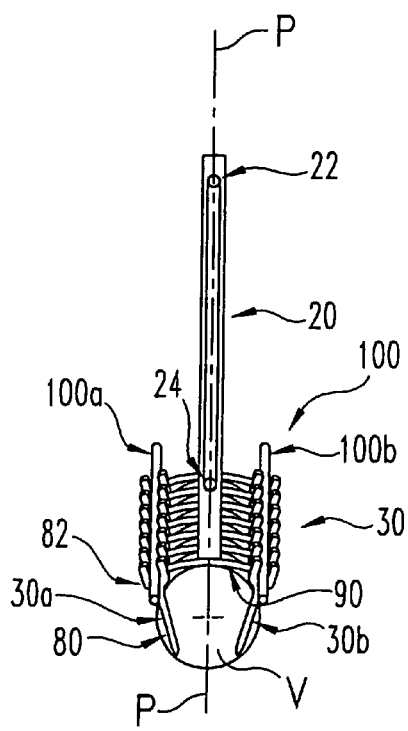
FIG. 26 is a schematical illustration of the alignment elements shown in FIG. 25, with a stabilization rod positioned along each side of the spinal column and engaged to the bone anchors to maintain the vertebrae in the corrected state.

In the illustrated embodiment of the invention, the bone anchors 30 are configured as bone screws having a threaded shank portion 80 and a head portion 82. In one embodiment of the invention, the bone screws are configured as pedicle screws, wherein the threaded shank portion 80 has a length and a thread configuration suitable for engagement within the pedicle region $P_v$ of the vertebra V. In the illustrated embodiment of the bone anchor 30, the head portion 82 is configured for engagement with a spinal rod (FIG. 26). In one specific embodiment, the head portion 82 defines a passage 84 sized to receive a spinal rod therein, with a fastener or setscrew (FIG. 27) extending through the head portion 82 and into engagement with the spinal rod to capture and secure the spinal rod within the passage 84. Additionally, the head portion 82 includes a pair of spaced apart arms 86a, 86b defining an open end which provide the head portion 82 with a top-loading, U-shaped configuration, with the fastener or setscrew engaged with internal threads formed along the spaced apart arms 86a, 86b. Further details regarding bone screws having a configuration similar to that of the bone screws illustrated in FIG. 17 are illustrated and described, for example, in U.S. Pat. No. 6,783,527 to Drewry et al., the contents of which are incorporated herein by reference.

However, it should be understood that other types and configuration of bone screws are also contemplated for use in association with the instrumentation 10, including, for example, bone screws having a closed head portion or a head portion defining a side-loading, C-shaped configuration. Additionally, other embodiments of bone screws are also contemplated which include a head portion configured as an unthreaded stem or shaft, with the spinal rod coupled to the unthreaded stem via a connector or coupling mechanism, an example of which is illustrated and described in U.S. Pat. No. 5,643,263 to Simonson or U.S. Pat. No. 5,947,967 to Barker, the contents of each patent reference incorporated herein by reference.

In still other embodiments of the invention, bone screws may be used in association with the instrumentation 10 which allow the head portion to be selectively pivoted or rotated relative to the threaded shank portion along multiple planes or about multiple axes. In one such embodiment, the head portion includes a receptacle for receiving a spherical-shaped portion of a threaded shank therein to allow the head portion to pivot or rotate relative to the threaded shank portion. A locking member or crown may be compressed against the spherical-shaped portion via a set screw or another type of fastener to lock the head portion at a select angular orientation relative to the threaded shank portion. Further details regarding one type of multi-axial screw suitable for use in association with the present invention are illustrated and described, for example, in U.S. Pat. No. 5,797,911 to Sherman et al., the contents of which are hereby incorporated herein by reference. The use of multi-axial bone anchors may be beneficial for use in the lower lumbar region of the spinal column, and particularly below the L4 vertebrae, where lordotic angles tend to be relatively high compared to other regions of the spinal column. Alternatively, in regions of the spine exhibiting relatively high intervertebral angles, the alignment elements 20, 20' and/or the bone anchors may be configured such that the alignment element may be coupled to the bone anchor at a fixed angle, such as, for example, via the use of an angled connector block or shim.

It should be understood that the bone screw embodiments illustrated and described herein are exemplary, and that other types and configurations of bone screws may also be used in association with the present invention, the likes of which would be apparent to one of ordinary skill in the art. It should also be understood that other types and configuration of bone anchors may be used in association with the present invention, including, for example, spinal hooks configured for engagement about a portion of a vertebra, bolts, pins, nails, clamps, staples and/or other types of bone anchor devices capable of being anchored in or to vertebral bone.

Referring to FIG. 18, shown therein is one embodiment of the invention wherein the bone anchors 30a, 30b are interconnected to one another via a bridge or link member 90 extending between the head portions 82 of the bone anchors 30a, 30b, with the alignment elements 20, 20' engaged to a central portion of the bridge members 90 to couple the alignment elements 20, 20' to the vertebrae V along a mid-portion of the spinal column, such as, for example, along the sagittal plane. Alternatively, the bridge member 90 may be engaged to other portions of the bone screws 30a, 30b, or may be engaged to other elements or structures extending from the head portions of the bone screw 30a, 30b. Additionally, the bridge member 90 may be outwardly curved to minimize interference with anatomic features of the vertebrae V and/or other anatomic structures. Positioning of the alignment elements 20, 20' in a medialized or central position relative to the bone anchors 30a, 30b results in distribution of the corrective forces exerted by the alignment elements 20, 20' across multiple locations on the vertebral body. As a result, stress concentrations are reduced at any single bone/implant interface as the correction forces are applied.

Furthermore, the bridge member 90 may be adjustable to accommodate for varying distances, varying angular orientations and/or misalignments between the bone screws 30a, 30b. Adjustment of the bridge member 90 may be provided via a rack-and-pinion adjustment mechanisms, telescoping adjustment mechanisms, turn buckle adjustment mechanisms, ball-and-socket mechanisms, pivoting mechanisms, hinge mechanisms, or any other suitable adjustment mechanism capable of accommodating for varying distances, varying angular orientations and/or misalignments between the bone screws 30a, 30b. As discussed above, the alignment element 20 includes an internally threaded passage 56 which may be threaded onto a threaded stem or projection associated with the bridge member 90, and the alignment element 20' includes an externally threaded stem or projection 56' which may be threaded into a threaded opening associated with the bridge member 90. However, as also discussed above, the alignment elements 20, 20' may be configured for releasable engagement with the bridge member 90 using other suitable connection techniques. Additionally, in other embodiments of the invention, one or more handles may be coupled to the bridge member 90 for manual application of manipulation or corrective forces to the vertebrae V.

Referring to FIG. 19, shown therein is another embodiment of the invention wherein the alignment elements 20, 20' are connected directly to a set of the bone screws 30a, 30b anchored along one side of the spinal column, and more specifically to the head portion 82 of the bone screws, to couple the alignment elements 20, 20' to the vertebrae V. By way of example, the arms 86a, 86b of the screw head portion 82 may define external threads configured for threading engagement with the internally threaded passage 56 of the alignment element 20 to releasably engage the alignment element 20 to one of the bone screws 30a, 30b. Alternatively, the arms 86a, 86b of the screw head portion 82 may define internal threads configured for threading engagement with the externally threaded stem 56' of the alignment element 20' to releasably engage the alignment element 20' to one of the bone screws 30a, 30b.

Referring now to FIGS. 20-25, shown therein are schematical illustrations of various stages of correction of an abnormal spinal curvature using the instrumentation 10. Although the alignment elements 20 are each shown as being positioned along a central or medial portion of the vertebrae V (as illustrated and described above with regard to FIG. 18), it should be understood that the alignment elements 20 may alternatively be positioned along either side of the vertebrae V (as illustrated and described above with regard to FIG. 19). It should further be understood that positioning of the alignment elements 20 along other portions of the vertebrae V is also contemplated as falling within the scope of the present invention. Additionally, although FIGS. 20-25 make specific reference to alignment elements 20, it should be understood that use of the alignments elements 20' or other embodiments of alignment elements is also contemplated as falling within the scope of the present invention.

Figure 20:
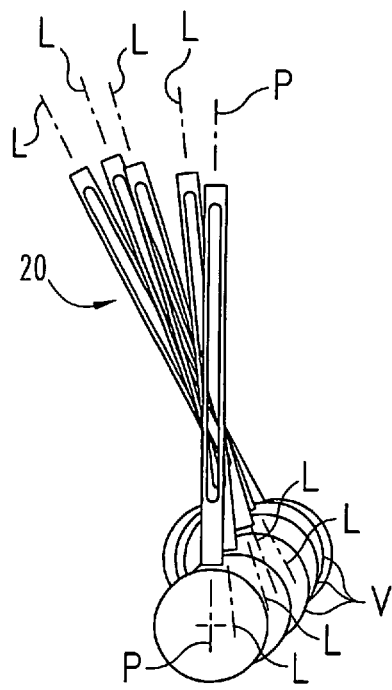
FIG. 20 is a schematical illustration of the scoliotic spine shown in FIG. 2 with the anteroposterior axes of the vertebrae positioned in an abnormal, non-coplanar state, and with alignment elements engaged to the vertebrae and arranged generally along the anteroposterior axes.

Referring initially to FIG. 20, shown therein is a number of the alignment elements 20 coupled to a corresponding number of vertebrae V. As indicated above, the alignment elements 20 may be engaged directly to a series of bone anchors 30 (FIG. 19) anchored along one side of the spinal column, or may be engaged to a bridge or link member extending between a pair of bilaterally-positioned bone anchors 30 anchored along each side of a corresponding vertebrae (FIG. 18). As also indicated above, the alignment elements 20 may alternatively be engaged directly to the vertebrae V.

As discussed above with regard to FIGS. 1 and 2, in a scoliotic spine, the natural physiological position and alignment of the vertebrae V are altered due to abnormal vertebral rotation and translation. As a result, the anteroposterior axes A-P of the vertebrae V, which are normally positioned within a common plane P (i.e., the sagittal plane), extend along multiple planes in a non-coplanar state. Additionally, in a scoliotic spine, the thoracic region of the spine is typically lordotic, thereby resulting in divergence between the anteroposterior axes A-P which is less than normal physiological divergence. Referring once again to FIG. 20, the alignment members 20 are initially positioned and arranged such that the longitudinal axes L of the alignment members 20 are positioned is substantial co-axial alignment with the non-corrected anteroposterior axes A-P of the vertebrae V. As a result, the longitudinal axes L of the alignment members 20 are initially not in alignment with one another along a common plane P, but instead extend along multiple planes in a non-coplanar configuration.

Figure 21:
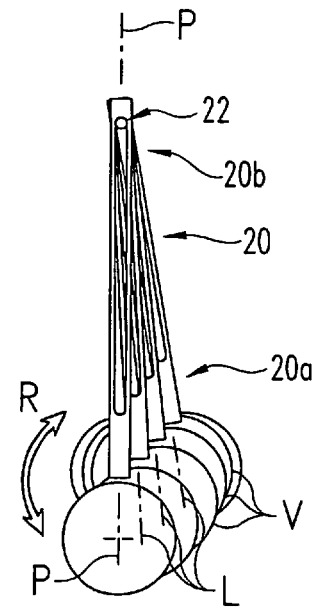
FIG. 21 is a schematical illustration of the alignment elements shown in FIG. 20, with a first reduction element engaged to the distal portions of the alignment elements to align the distal portions generally along the transverse axis of the first reduction element and resulting in derotation of one or more of the vertebrae toward a corrected state.

Referring to FIG. 21, the distal portions 20b of the alignment elements 20 are drawn together in general alignment with one another and the first reduction rod 22 is inserted through the distal end portions of each of the slots 54 in the alignment elements 20. In order to facilitate alignment of the distal portions 20b with one another, the alignment elements 20 may be manually grasped and manipulated by the surgeon and/or an instrument or tool may be used to exert a lateral or torsional force onto one or more of the alignment elements 20. However, in another embodiment, general alignment of the distal portions 20b with one another may be accomplished by inserting the reduction rod 22 into central portions of the slots 54, which may initially be in closer alignment with one another compared to the distal end portions of the slots. Once inserted into the central portions of the slots 54, the first reduction rod 22 may be axially displaced through the slots 54 in a distal direction, which in turn draws the distal portions 20b of the alignment elements 20 into general alignment with one another via the exertion of lateral forces onto the inner side surfaces of the alignment elements 20 which define the slots 54. Various instruments may be used to facilitate axial displacement of the first reduction rod 22 through the slots 54, the likes of which will be discussed in greater detail below with regard to the second reduction rod 24. Initial introduction of the first reduction rod 22 into the slots 54 may be facilitated via the use of a surgical mallet, a slap hammer, or by any other suitable tool or instrument.

The first reduction rod 22 cooperates with the alignment elements 20 to maintain alignment of the distal portion 20b generally along the first transverse axis $T_1$ (FIG. 3), with the first transverse axis $T_1$ preferably extending along the sagittal plane P. Alignment of the distal portions 20b of the alignment elements 20 generally along the first transverse axis $T_1$ correspondingly imparts rotational movement to one or more of the alignment elements 20. Rotation of the alignment elements 20 in turn imparts a rotational force onto the corresponding vertebrae V to derotate the vertebrae V generally along the transverse plane in the direction of arrow R. It should be understood that the direction of derotation is dependent on the particular characteristics of the spinal deformity being treated, and may occur in a clockwise direction and/or a counter-clockwise direction. It should further be understood that bringing the distal portions 20b into general alignment with one another may not result in rotation of one or more of the alignment elements 20, in which case the corresponding vertebrae V will not be rotationally affected. Although alignment of the distal portions 20b of the alignment elements 20 partially reduces the spinal deformity, further correction is required.

Figure 22:
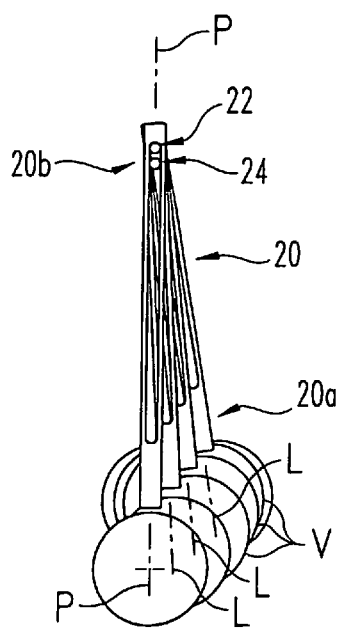
FIG. 22 is a schematical illustration of the alignment elements shown in FIG. 21, with a second reduction element engaged to the distal portions of the alignment elements.

Referring to FIG. 22, the second reduction rod 24 is inserted through the distal end portions of each of the slots 54 in the alignment elements 20 adjacent the first reduction rod 22. Since the distal end portions of the slots 54 are maintained in general alignment with one another via the first reduction rod 22, insertion of the second reduction rod 24 into the slots 54 should not require significant manipulation of the alignment elements 20. However, introduction of the second reduction rod 24 into the slots 54 may be facilitated via the use of a surgical mallet, a slap hammer, or by any other suitable tool or instrument.

Figure 23:
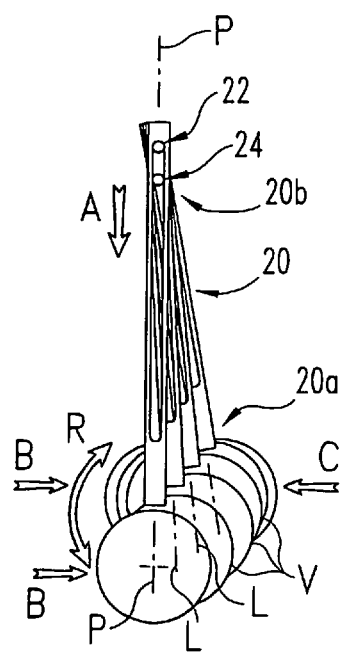
FIG. 23 is a schematical illustration of the alignment elements shown in FIG. 22, showing sliding engagement of the second reduction element along the alignment elements in a proximal direction to translate and derotate one or more of the vertebrae toward a corrected state.

Referring now to FIG. 23, with the first reduction rod 22 remaining in a substantially stationary position to maintain the distal portions 20b in general alignment with one another, the second reduction rod 24 is proximally displaced through the slots 54 in the alignment elements 20 in the direction of arrow A, away from the first reduction rod 22 and generally along the plane P. Displacement of the second reduction rod 24 through the slots 54 may be facilitated via the use of a surgical mallet, a rod pusher or persuader, a distractor device engaged between the second reduction rod 24 and another element (such as the first reduction rod 22) to distract the second reduction rod 24 in a proximal direction away from the first reduction rod 22, or by any other suitable tool or instrument. The tools or instruments used to displace the second reduction rod 24 through the slots 54 may be manually driven or may be powered. Additionally, the tools or instruments may be incrementally advanced in a controlled manner to provide incremental displacement of the second reduction rod 24 through the slots 54 in the alignment elements 20. Such incremental advancement may be provided by way of a rack-and-pinion type drive, a ratcheting drive, a turnbuckle mechanism, or by any other suitable drive or advancement mechanism.

Sliding engagement of the second reduction rod 24 through the slots 54 in turn draws the alignment elements 20 toward one another via the exertion of lateral forces onto the inner side surfaces of the alignment elements 20. Specifically, as the second reduction rod 24 is proximally displaced through the slots 54, one or more of the alignment elements 20 is correspondingly rotated about the first reduction rod 22 toward the sagittal plane P. Rotation of the alignment elements 20 in turn imparts a rotational force onto the corresponding vertebrae V to provide further derotation of the vertebrae V generally along the transverse plane in the direction of arrow R which, as discussed above, may occur in a clockwise direction and/or a counter-clockwise direction.

Additionally, sliding engagement of the second reduction rod 24 through the slots 54 (and rotation of the alignment elements 20 about the first reduction rod 22) also imparts a lateral force onto the corresponding vertebrae V, which in turn results in relative translational movement of the vertebrae V generally along the coronal plane in the directions of arrow B and/or arrow C. It should be understood that the direction of translational movement of the vertebrae V is dependent on the particular spinal deformity being treated, and may occur in either or both of the directions of arrows B and C. It should also be understood that proximal displacement of the second reduction rod 24 through the slots 54 may not result in rotation of one or more of the alignment elements 20, in which case the corresponding vertebrae V will not be rotationally or translationally affected. It should further be understood that derotation of the vertebrae V in the direction of arrow R and translation of the vertebrae V in the direction of arrows B and C results in a reduction of the misalignment of the vertebrae V along both the transverse and coronal planes.

Figure 24:
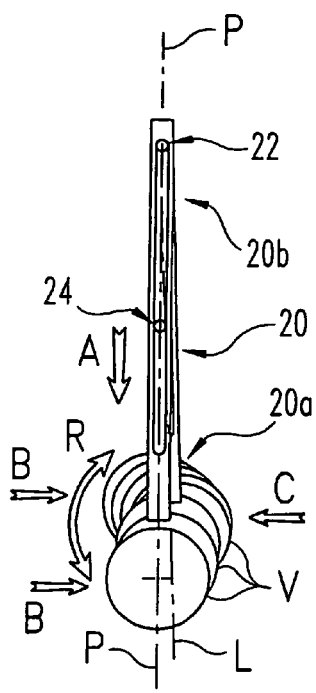
FIG. 24 is a schematical illustration of the alignment elements shown in FIG. 23, showing further sliding engagement of the second reduction element along the alignment elements in a proximal direction to further translate and derotate one or more of the vertebrae toward a corrected state.
Figure 25:
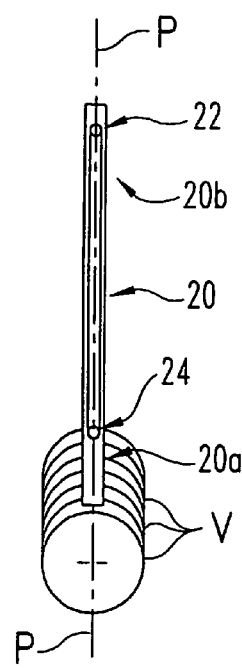
FIG. 25 is a schematical illustration of the alignment elements shown in FIG. 24, showing positioning of the second reduction element at a location adjacent the proximal portions of the alignment elements to align the proximal portions generally along the transverse axis of the second reduction element and resulting in translation and derotation of the vertebrae to the corrected state.

Referring to FIG. 24, further proximal displacement of the second reduction rod 24 through the slots 54 in the alignment elements 20 results in additional derotation of the vertebrae V generally along the transverse plane in the direction of arrow R, and additional translation movement of the vertebrae V generally along the coronal in the directions of arrows B and C. Referring to FIG. 25, the second reduction rod 24 is further displaced through the slots 54 to apposition adjacent the proximal portions 20a of the alignment elements 20. In this position, the proximal portions 20a are drawn into general alignment with one another along the second transverse axis $T_2$, with the second transverse axis $T_2$ preferably arranged and extending generally along the sagittal plane P. With the distal portions 20b of the alignment elements 20 maintained in general alignment along the transverse axis $T_1$ via the first reduction rod 22, and with the proximal portions 20a drawn into general alignment with one another along the second transverse axis $T_2$ via displacement of the second reduction rod 24, the longitudinal axes L of the alignment elements 20 are resultingly positioned in general alignment with one another in a co-planar relationship along the sagittal plane P. General alignment of the alignment elements 20 along the sagittal plane P in turn results in general alignment of the anteroposterior axes A-P of the vertebrae V along the sagittal plane P, thereby reducing the spinal deformity via correcting misalignment of the vertebrae V along both the coronal and transverse planes.

Referring once again to FIG. 3, alignment of the vertebrae V along the sagittal plane is accomplished via the spacer elements 26 and the block elements 28. In one embodiment, the block elements 28 are assembled with the outer alignment elements 20o prior to fill displacement of the second reduction rod 24 through the slots 54. The outer alignment elements 20o are in turn anchored to the outer vertebrae Vo which define the outer ends or boundaries of at least a portion of the spinal curvature being treated. As discussed above with regard to FIG. 16, the block elements 28 are engaged with the outer alignment elements 20 in such a manner as to arrange the tapered engagement surface 74 in general alignment with the slot 54 in the alignment element 20. As also discussed above, each of the block elements 28 have a block height $h_b$ and a taper angle θ that are selected based on the particular characteristics of the portion of the spinal column being treated. As further discussed above, although the illustrated embodiment of the invention utilizes two block elements 28 in association with the outer alignment elements 20o, it should be understood that additional block elements 28 may be used in association with one or more of the other alignment elements 20 as well.

With the block elements 28 assembled with the outer alignment elements 20o, the second reduction rod 24 is proximally displaced into abutting engagement against the tapered surfaces 74 of the block elements 28. Compression of the second reduction rod 24 onto the tapered surface 74 in turn results in positioning of the outer alignment elements 20o and the corresponding outer vertebra Vo at a select height and at a select angular orientation relative to one another, which preferably corresponds to the normal physiological height and angular orientation (e.g., the natural kyphosis angle) of the outermost vertebrae Vo along the sagittal plane. The block elements 28 allow relative translation (e.g., sinking) of the outer vertebrae Vo along the sagittal plane to position the outer vertebrae Vo at a substantially normal physiological height, and also allow relative rotation of the outer vertebrae Vo along the sagittal plane to position the outer vertebrae Vo at a substantially normal physiological angle β.

With the outer vertebrae Vo positioned at the correct physiological height and anatomic angle, positioning of the remaining vertebrae V into correct alignment along the sagittal plane is accomplished via engagement of the spacer elements 26 between adjacent pairs of alignment elements 20p. As indicated above, the spacer elements 26 may be provided with a fixed configuration defining a select spacer length l, or may be provided with a variable configuration wherein the overall length of the spacer may be adjusted to a select spacer length l, either pre-operatively or intra-operatively. In either case, the spacer elements 26 are engaged between the distal portions 20b of adjacent pairs of the elongate alignment elements 20p to space the adjacent distal portions 20b apart at a select distance d. With the proximal portions 20a of the adjacent pair of alignment elements 20p securely coupled to the adjacent vertebrae Vp, spacing the distal portions 20b apart at a select distance d correspondingly positions the adjacent pairs of vertebrae Vp at an angle α substantially corresponding to the normal physiological angular orientation of the adjacent vertebrae Vp along the sagittal plane.

Referring to FIG. 26, following reduction of the spinal deformity and final adjustment of the vertebrae V, one or more elongate implants 100 are engaged to the bone anchors 30 to maintain the vertebrae V in the corrected state. In the illustrated embodiment, the elongate implant 100 is configured as a spinal rod. However, other types and configurations of elongate implants are also contemplated, such as, for example, a spinal plate, a bar, a cable, a tether, or any other suitable elongate implant capable of maintaining the vertebrae V in the corrected state. In the illustrated embodiment, the elongate implant 100 is secured to the bone anchors 30. However, in other embodiments, the elongate element 100 may be engaged directly to the vertebrae V, which may be particularly appropriate if the elongate element is configured as a plate or tether. In one embodiment, the elongate implant 100 is formed of a biocompatible material, such as, for example, stainless steel or titanium. However, other materials are also contemplated, including, for example, titanium alloys, metallic alloys such as chrome-cobalt, polymer based materials such as PEEK, composite materials, or any other suitable material that would occur to one of skill in the art.

In the illustrated embodiment of the invention, a pair of spinal rods 100a, 100b are positioned along the spinal column, with one of the spinal rods 100a positioned within the head portions 82 of the bone anchors 30a along one side of the spinal column, and the other spinal rod 100b positioned within the head portions 82 of the bone anchors 30b along the opposite side of the spinal column. The spinal rods 100a, 100b may be bent or contoured, either outside of the patient's body or in-situ, to more closely match the position, orientation and alignment of the bone anchors 30a, 30b.

Figure 27:
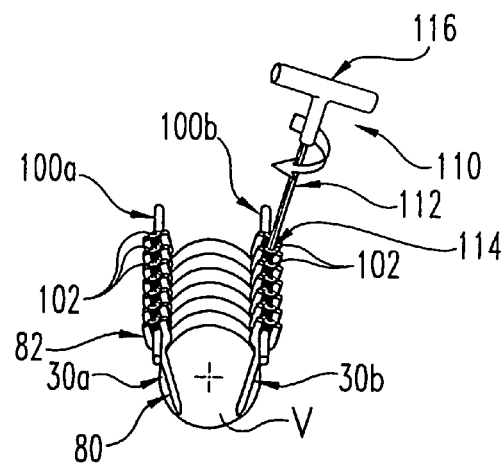
FIG. 27 is a schematical illustration of the stabilization rods securely engaged to the bone anchors by a number of lock member to secure the vertebrae in the corrected state, and with the alignment elements, the first and second reduction elements, and the bridge members removed from the patient's body.

As shown in FIG. 27, the spinal rods 100a, 100b are engaged to the bone anchors 30a, 30b via a number of lock members 102, such as, for example, set screws, to capture the spinal rods 100a, 100b within the head portions 82. In one embodiment, the set screws 102 may be threadingly engaged with the head portions 82 of the bone anchors 30a, 30b via a driving tool 110 to maintain the spinal rods 100a, 100b in engagement with the bone anchors 30a, 30b. In one embodiment, the driving tool 110 includes a drive shaft 112 including a distal end portion 114 that is positioned within a tool receiving recess in the set screw, and a handle 116 for imparting rotational force onto the drive shaft 112.

Prior to final tightening of the set screws 102, the reduction rods 22 and 24 may be removed from the alignment elements 20 and final adjustments can be made to individual vertebrae V by manual manipulation of one or more of the alignment elements 20 to correct any remaining misalignments between the vertebrae V. The set screw 102 are then tightened into firm engagement with the spinal rods 100a, 100b, thereby securely capturing the spinal rods 100a, 100b within the bone anchors 30a, 30b to maintain the vertebrae V in the corrected state. Once the spinal rods 100a, 100b are secured to the bone anchors 30a, 30b, the remaining elements of the instrumentation 10 may be removed from the patient's body. Additionally, various types of transverse connectors (not shown) may be coupled between the spinal rods 100a, 100b to provide additional stabilization and support to the rod system. Blood supply is restored to the arthrodesis area and grafting may used to facilitate arthrodesis between adjacent vertebrae to further stabilize the spinal column.

As illustrated and described above with regard to FIG. 19, in another embodiment of the invention, the alignment elements 20 may be connected directly to the bone anchors 30a, 30b along one side of the spinal column. In such an embodiment, the spinal deformity is reduced via a technique similar to that described above. However, instead of positioning the instrumentation 10 along a central or medial portion of the spinal column (e.g., generally along the sagittal plane), the instrumentation is positioned along one side of the spinal column via engagement with a first set of the bone anchors 30a, 30b. Upon reduction of the spinal deformity, an elongate implant, such as a spinal rod, may be engaged to the second set of bone anchors 30a, 30b anchored along the opposite side of the spinal column to secure the vertebrae in the corrected state. The instrumentation 10 is thereafter disengaged from the first set of bone anchors 30a, 30b, followed by engagement of a second elongate implant to the first set of bone anchors 30a, 30b to further secure the vertebrae in the corrected state.

As should now be apparent, the instrumentation 10 illustrated and described above may be used to treat a spinal deformity via a reduction technique which addresses both rotational and translational aspects of the deformity along all three spatial planes, including the coronal plane, the transverse plane, and the sagittal plane. While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of reducing a spinal deformity, comprising:
   providing a plurality of elongate elements and first and second reduction elements, each of the elongate elements extending along a longitudinal axis and including a proximal portion and a distal portion;

coupling the proximal portions of the elongate elements to respective vertebrae;
engaging the first reduction element with the elongate elements to maintain the distal portions of the elongate elements in general alignment relative to a first transverse axis extending along a length of the first reduction element;
engaging the second reduction element with the elongate elements;
displacing the second reduction element in a proximal direction to generally align the proximal portions of the elongate elements relative to the second reduction element, and wherein the displacing of the second reduction element in the proximal direction causes at least one of the elongate elements to rotate about the first transverse axis of the first reduction element to reduce the spinal deformity;
wherein the displacing of the second reduction element in the proximal direction occurs during the maintaining of the distal portions of the elongate elements in general alignment along the first transverse axis of the first reduction element;
anchoring a pair of bone anchors to each of a plurality of vertebrae defining the spinal deformity; and
interconnecting the pair of bone anchors with a bridge member,
wherein the coupling comprises engaging the elongate elements to respective ones of the bridge member.

2. The method of claim 1, wherein the displacing of the second reduction element results in translational movement of at least one of the vertebrae to reduce the spinal deformity.

3. The method of claim 2, wherein the first reduction element maintains the distal portions of the elongate elements in general alignment along the first transverse axis of the first reduction element, wherein the second reduction element generally aligns the proximal portions of the elongate elements along a second transverse axis of the second reduction element; and
wherein the first transverse axis and the second transverse axis are generally positioned within and extend parallel with a common plane subsequent to the displacing.

4. The method of claim 3, wherein the common plane comprises a sagittal plane.

5. The method of claim 2, wherein the elongate elements are positioned in general alignment with one another substantially within and parallel with a common plane subsequent to the displacing, wherein the common plane comprises a sagittal plane.

6. The method of claim 1, wherein maintaining the distal portions of the elongate elements in general alignment along the first reduction element while displacing the second reduction element in a proximal direction results in positioning of the elongate elements substantially within and parallel with a common plane.

7. The method of claim 6, wherein the first reduction element maintains the distal portions of the elongate elements in general alignment along the first transverse axis of the first reduction element, wherein the second reduction element generally aligns the proximal portions of the elongate elements along a second transverse axis of the second reduction element; and
wherein the first transverse axis and the second transverse axis are generally positioned within and extend parallel with the common plane subsequent to the displacing.

8. The method of claim 7, wherein the common plane comprises a sagittal plane.

9. The method of claim 6, wherein the common plane comprises a sagittal plane.

10. The method of claim 1, wherein each of the elongate elements defines a slot having a length extending between the proximal and distal portions; and
further comprising positioning the second reduction element within the slots of the elongate elements and displacing the second reduction element along the slots in a proximal direction to generally align the proximal portions along the second reduction element to reduce the spinal deformity.

11. The method of claim 1, further comprising establishing a select distance between the distal portions of adjacent pairs of the elongate elements to arrange the adjacent pairs of the elongate elements at a select angle relative to one another to correspondingly position the vertebrae to which the adjacent pairs of elongate elements are coupled substantially at the select angle.

12. The method of claim 1, further comprising establishing a select distance between the distal portions of adjacent pairs of the elongate elements to arrange the adjacent pairs of the elongate elements at a select angle relative to one another to correspondingly position the vertebrae to which the adjacent pairs of elongate elements are coupled substantially at the select angle; and
wherein the establishing of the select distance is accomplished by positioning a spacer element having a select length between the distal portions of the adjacent pairs of the elongate elements.

13. The method of claim 12, wherein the spacer element is engaged with the first reduction element.

14. The method of claim 12, wherein the displacing of the second reduction element in the proximal direction causes at least one of the elongate elements to rotate about the first transverse axis of the first reduction element to reduce the spinal deformity.

15. The method of claim 12, wherein the first reduction element maintains the distal portions of the elongate elements in general alignment along the first transverse axis of the first reduction element, wherein the second reduction element generally aligns the proximal portions of the elongate elements along a second transverse axis of the second reduction element; and
wherein the first transverse axis and the second transverse axis are generally positioned within and extend parallel with a common plane subsequent to the displacing.

16. The method of claim 15, wherein the common plane comprises a sagittal plane.

17. The method of claim 12, wherein the elongate elements are positioned in general alignment with one another substantially within and parallel with a common plane subsequent to the displacing.

18. The method of claim 17, wherein the common plane comprises a sagittal plane.

19. The method of claim 1, further comprising arranging at least two of the elongate elements at a select angle relative to one another to correspondingly position the vertebrae to which the at least two of the elongate elements are coupled substantially at the select angle.

20. The method of claim 19, wherein the arranging is accomplished by engaging the second reduction rod against a tapered surface associated with each of the at least two elongate elements.

21. The method of claim 1, further comprising:
anchoring at least one bone anchor to each of a plurality of vertebrae defining the spinal deformity; and wherein the coupling comprises engaging the elongate elements to corresponding ones of the at least one bone anchor.

22. The method of claim 1, wherein the pair of bone anchors are positioned on opposite sides of the spinal column; and
wherein the elongate elements are positioned along a midportion of the spinal column.

23. The method of claim 22, further comprising engaging a pair of elongate rods with the bone anchors along each side of the spinal column to maintain correction of the spinal deformity.

24. The method of claim 1, wherein the coupling of the elongate elements comprises anchoring of the elongate elements directly to the respective vertebrae.

25. The method of claim 1, wherein reducing the spinal deformity comprises at least one of rotating and translating the effected vertebrae along three spatial planes.

26. The method of claim 25, wherein the three spatial planes comprise the transverse plane, the coronal plane and the sagittal plane.

27. The method of claim 1, wherein the first reduction element maintains the distal portions of the elongate elements in general alignment along the first transverse axis of the first reduction element, wherein the second reduction element generally aligns the proximal portions of the elongate elements along a second transverse axis of the second reduction element; and
wherein the first transverse axis and the second transverse axis are generally positioned within and extend parallel with a common plane subsequent to the displacing.

28. The method of claim 27, wherein the common plane comprises a sagittal plane.

29. The method of claim 1, wherein the elongate elements are positioned in general alignment with one another substantially within and parallel with a common plane subsequent to the displacing, wherein the common plane comprises a sagittal plane.

30. The method of claim 1, wherein the displacing during the maintaining results in positioning of the elongate elements substantially within and parallel with a common plane.

31. The method of claim 30, wherein the common plane comprises a sagittal plane.

32. A method of reducing a spinal deformity, comprising:
providing a plurality of elongate elements, each of the elongate elements extending along a longitudinal axis and including a proximal portion and a distal portion;
coupling the proximal portions of the elongate elements to respective vertebrae;
aligning the distal portions of the elongate elements generally along a first transverse axis extending through said distal portions;
aligning the proximal portions of the elongate elements generally along a second transverse axis while maintaining alignment of the distal portions along the first transverse axis to reduce the spinal deformity wherein the aligning of the proximal portions occurs during the maintaining of the distal portions, and wherein the aligning of the proximal portions of the elongate elements generally along the second transverse axis causes at least one of the elongate elements to rotate about the first transverse axis;
anchoring a pair of bone anchors to each of a plurality of vertebrae defining the spinal deformity; and
interconnecting the pair of bone anchors with a bridge member;
wherein the coupling comprises engaging the elongate elements to respective ones of the bridge member.

33. The method of claim 32, further comprising:
engaging a first reduction element with the elongate elements to maintain alignment of the distal portions generally along the first transverse axis; and
engaging a second reduction element with the elongate elements to maintain alignment of the proximal portions generally along the second transverse axis.

34. The method of claim 33, wherein the aligning of the proximal portions of the elongate elements generally along the second transverse axis results from slidably displacing the second reduction element in a proximal direction along the elongate elements during the maintaining of the alignment of the distal portions along the second transverse axis.

35. The method of claim 34, wherein the displacing of the second reduction element imparts rotational movement to at least some of the elongate elements about the first transverse axis of the first reduction element which results in at least one of rotational and translation movement of the corresponding vertebrae to reduce the spinal deformity.

36. The method of claim 32, wherein the aligning of the distal portions of the elongate elements generally along the first transverse axis and the aligning of the proximal portions of the elongate elements generally along the second transverse axis results in positioning of the elongate elements substantially within and parallel with a common plane, wherein the common plane comprises a sagittal plane.

37. The method of claim 32, wherein each of the elongate elements defines a slot having a length extending between the proximal and distal portions; and
further comprising positioning the second reduction element within the slots of the elongate elements and displacing the second reduction element along the slots in a proximal direction to generally align the proximal portions along the second reduction element to reduce the spinal deformity.

38. The method of claim 32, further comprising establishing a select distance between the distal portions of adjacent pairs of the elongate elements to arrange the adjacent pairs of the elongate elements at a select angle relative to one another to correspondingly position the vertebrae to which the adjacent pairs of elongate elements are coupled substantially at the select angle.

39. The method of claim 32, further comprising arranging at least two of the elongate elements at a select angle relative to one another to correspondingly position the vertebrae to which the at least two of the elongate elements are coupled substantially at the select angle.

40. The method of claim 1 wherein the pair of bone anchors are positioned on opposite sides of the spinal column; and
wherein the elongate elements are positioned along a midportion of the spinal column.

41. The method of claim 32, wherein reducing the spinal deformity comprises at least one of rotating and translating the effected vertebrae along three spatial planes.

42. The method of claim 32, wherein the aligning of the proximal portions during the maintaining results in positioning of the elongate elements substantially within and parallel with a common plane.

43. The method of claim 42, wherein the common plane comprises a sagittal plane.

44. The method of claim 32, wherein the first transverse axis and the second transverse axis are generally positioned within and extend parallel with a common plane following the aligning.

45. The method of claim 44, wherein the common plane comprises a sagittal plane.

46. A method of reducing a spinal deformity, comprising:
providing a plurality of elongate elements and first and second reduction elements, each of the elongate elements extending along a longitudinal axis and including a proximal portion and a distal portion;
coupling the proximal portions of the elongate elements to respective vertebrae;
engaging the first reduction element with the elongate elements to maintain the distal portions of the elongate elements in general alignment relative to the first reduction element;
engaging the second reduction element with the elongate elements;
displacing the second reduction element in a proximal direction to generally align the proximal portions of the elongate elements relative to the second reduction element, and wherein the displacing of the second reduction element in the proximal direction causes at least one of the elongate elements to rotate about the first reduction element to reduce the spinal deformity;
wherein the elongate elements are positioned in general alignment with one another substantially within and parallel with a common plane subsequent to the displacing, wherein the common plane comprises a sagittal plane;
anchoring a pair of bone anchors to each of a plurality of vertebrae defining the spinal deformity; and
interconnecting the pair of bone anchors with a bridge member;
wherein the coupling comprises engaging the elongate elements to respective ones of the bridge member.

47. The method of claim 46, wherein the displacing of the second reduction element in the proximal direction occurs during the maintaining of the distal portions of the elongate elements in general alignment along the first reduction element.

48. A method of reducing a spinal deformity, comprising:
providing a plurality of elongate elements and first and second reduction elements, each of the elongate elements extending along a longitudinal axis and including a proximal portion and a distal portion;
coupling the proximal portions of the elongate elements to respective vertebrae;
engaging the first reduction element with the elongate elements to maintain the distal portions of the elongate elements in general alignment relative to the first reduction element;
engaging the second reduction element with the elongate elements;
displacing the second reduction element in a proximal direction to generally align the proximal portions of the elongate elements relative to the second reduction element;
wherein the displacing of the second reduction element imparts rotational movement to at least some of the elongate elements about the first reduction element which results in at least one of rotational and translation movement of the corresponding vertebrae to reduce the spinal deformity;
wherein the elongate elements are positioned in general alignment with one another substantially within and parallel with a common plane subsequent to the displacing, wherein the common plane comprises a sagittal plane;
anchoring a pair of bone anchors to each of a plurality of vertebrae defining the spinal deformity; and
interconnecting the pair of bone anchors with a bridge member,
wherein the coupling comprises engaging the elongate elements to respective ones of the bridge member.

49. The method of claim 48, wherein the displacing of the second reduction element in the proximal direction occurs during the maintaining of the distal portions of the elongate elements in general alignment along the first reduction element.

50. A method of reducing a spinal deformity, comprising:
providing a plurality of elongate elements and first and second reduction elements, each of the elongate elements extending along a longitudinal axis and including a proximal portion and a distal portion;
coupling the proximal portions of the elongate elements to respective vertebrae;
engaging the first reduction element with the elongate elements to maintain the distal portions of the elongate elements in general alignment relative to the first reduction element;
engaging the second reduction element with the elongate elements; and
displacing the second reduction element in a proximal direction to generally align the proximal portions of the elongate elements relative to the second reduction element to reduce the spinal deformity;
wherein maintaining the distal portions of the elongate elements in general alignment along the first reduction element while displacing the second reduction element in a proximal direction results in positioning of the elongate elements substantially within and parallel with a common plane, wherein the common plane comprises a sagittal plane;
anchoring a pair of bone anchors to each of a plurality of vertebrae defining the spinal deformity; and
interconnecting the pair of bone anchors with a bridge member;
wherein the coupling comprises engaging the elongate elements to respective ones of the bridge member.

51. The method of claim 50, wherein the displacing of the second reduction element in the proximal direction occurs during the maintaining of the distal portions of the elongate elements in general alignment along the first reduction element.

52. A method of reducing a spinal deformity, comprising:
providing a plurality of elongate elements, each of the elongate elements extending along a longitudinal axis and including a proximal portion and a distal portion;
coupling the proximal portions of the elongate elements to respective vertebrae;
aligning the distal portions of the elongate elements generally along a first transverse axis;
aligning the proximal portions of the elongate elements generally along a second transverse axis while maintaining alignment of the distal portions to reduce the spinal deformity, and wherein the aligning of the proximal portions of the elongate elements generally along the second transverse axis causes at least one of the elongate elements to rotate about the first transverse axis;
wherein the aligning of the distal portions of the elongate elements generally along the first transverse axis and the aligning of the proximal portions of the elongate elements generally along the second transverse axis results in positioning of the elongate elements substantially within and parallel with a common plane, wherein the common plane comprises a sagittal plane;

anchoring a pair of bone anchors to each of a plurality of vertebrae defining the spinal deformity; and
interconnecting the pair of bone anchors with a bridge member;
wherein the coupling comprises engaging the elongate elements to respective ones of the bridge member.

* * * * *